US012703678B2

(12) United States Patent
Lau et al.

(10) Patent No.: US 12,703,678 B2
(45) Date of Patent: Aug. 11, 2026

(54) PROCESS FOR PRODUCING 1,5-PENTAMETHYLENE DIISOCYANATE FROM CADAVERINE SALT

(71) Applicant: MOJIA BIOTECH LTD., Guang'an City (CN)

(72) Inventors: Man Kit Lau, Shanghai (CN); Chengliang Lu, Shanghai (CN); Ansen Chiew, Shanghai (CN)

(73) Assignee: MOJIA BIOTECH LTD., Guang'an City (CN)

( * ) Notice: Subject to any disclaimer, the term of this patent is extended or adjusted under 35 U.S.C. 154(b) by 513 days.

(21) Appl. No.: 18/031,039

(22) PCT Filed: Oct. 9, 2021

(86) PCT No.: PCT/CN2021/122833

§ 371 (c)(1),
(2) Date: Apr. 10, 2023

(87) PCT Pub. No.: WO2022/073506

PCT Pub. Date: Apr. 14, 2022

(65) Prior Publication Data

US 2023/0416194 A1 Dec. 28, 2023

(30) Foreign Application Priority Data

Oct. 10, 2020 (WO) ................ PCT/CN2020/120154

(51) Int. Cl.
*C07C 265/14* (2006.01)

(52) U.S. Cl.
CPC .................................. *C07C 265/14* (2013.01)

(58) Field of Classification Search
CPC ... C07C 265/14; C07C 263/04; C07C 269/04; C07C 271/04; C07C 263/10; C12P 13/001
See application file for complete search history.

(56) References Cited

U.S. PATENT DOCUMENTS 9,234,069 B2 1/2016 Nakagawa et al.
9,371,413 B2 6/2016 Nakagawa et al.
(Continued)

FOREIGN PATENT DOCUMENTS

CN 101495643 A 7/2009
CN 101928235 12/2010
(Continued)

OTHER PUBLICATIONS

International Search Report for PCT/CN2021/122833, mailed mailed Jan. 7, 2022.

(Continued)

*Primary Examiner* — Deborah D Carr
(74) *Attorney, Agent, or Firm* — Hoffmann & Baron, LLP

(57) ABSTRACT

An improved process for producing 1,5-pentamethylene diisocyanate (PDI) from a cadaverine salt is described herein. The process generally comprises providing a solution comprising a cadaverine salt dissolved in an inert solvent in the presence of a tertiary amine base; and subjecting the solution to a liquid-phase phosgenation reaction to convert the cadaverine to PDI. The phosgenation reaction comprises a step of maintaining the reaction at temperatures between 100° C. and 120° C. for a sufficient time to achieve a desired threshold yield of PDI. The processes described herein enable reductions in the amounts of reactants consumed, reaction temperatures, and/or overall reaction time, as compared to conventional phosgenation reactions. Employing a bio-based cadaverine salt that was not previously subjected to distillation is found to be advantageous, since subjecting cadaverine to high temperatures leads to the formation of certain cyclic compounds that are carried over to the PDI produced.

20 Claims, 7 Drawing Sheets

Specification includes a Sequence Listing.

(56) References Cited

U.S. PATENT DOCUMENTS

| | | | |
|---|---|---|---|
| 9,376,404 | B2 | 6/2016 | Nakagawa et al. |
| 10,053,419 | B2 | 8/2018 | Yoshimoto et al. |
| 10,112,892 | B2 | 10/2018 | Arras et al. |
| 10,173,970 | B2 | 1/2019 | Sanders et al. |
| 10,329,248 | B2 | 6/2019 | Sanders et al. |
| 10,457,632 | B2 | 10/2019 | Miyamoto et al. |
| 2002/0123644 | A1 | 9/2002 | Kitai et al. |
| 2013/0338330 | A1 | 12/2013 | Nakagawa et al. |
| 2016/0083503 | A1 | 3/2016 | Nakagawa et al. |
| 2016/0090368 | A1 | 3/2016 | Nakagawa et al. |
| 2017/0283370 | A1 | 10/2017 | Sanders et al. |
| 2018/0179150 | A1 | 6/2018 | Arras et al. |
| 2019/0112259 | A1 | 4/2019 | Sanders et al. |
| 2021/0380528 | A1 | 12/2021 | Takamatsu et al. |

FOREIGN PATENT DOCUMENTS

| | | | |
|---|---|---|---|
| CN | 102260194 | A | 11/2011 |
| CN | 102702028 | B | 10/2012 |
| CN | 106045882 | A | 10/2016 |
| CN | 106431991 | A | 2/2017 |
| CN | 106496072 | A | 3/2017 |
| CN | 106883150 | A | 6/2017 |
| CN | 107337615 | A | 11/2017 |
| CN | 109369457 | A | 2/2019 |
| DE | 2625075 | A1 | 12/1977 |
| EP | 3235804 | A1 | 10/2017 |
| GB | 566532 | A | 1/1945 |
| GB | 1077031 | A | 7/1967 |
| JP | 2012152202 | A | 8/2012 |
| WO | 2014/114000 | A1 | 7/2014 |

OTHER PUBLICATIONS

Written Opinion of the International Searching Authority in PCT/CN2021/122833, mailed Jan. 7, 2022.

Callison et al., "Origin of Impurities Formed in a Polyurethane Production Chain. Part 2: A Route to the Formation of Colored Impurities", Industrial & Engineering Chemistry Research (2012), 51, 11021-11030.

Cotarca et al., "Bis(trichloromethyl)carbonate (BTC, Triphosgene): A Safer Alternative to Phosgene?", Organic Process Research & Development (2017), 21: 1439-1446.

Kreye et al., "Sustainable routes to polyurethane precursors", Green Chemistry (2013), 15: 1431-1455.

Fig. 1

$H_2N$–(CH₂)–$NH_2$ 2HCl → OCN–(CH₂)–NCO

Gas chromatogram for Example 14

Gas chromatogram for Example 16

Gas chromatogram for Example 38

Gas chromatogram for Example 39

Gas chromatogram for Example 41

Gas chromatogram for Example 44

PROCESS FOR PRODUCING 1, 5-PENTAMETHYLENE DIISOCYANATE FROM CADAVERINE SALT

CROSS REFERENCE TO RELATED APPLICATIONS

The present application is a National Stage Application claiming the priority of co-pending PCT Application No. PCT/CN2021/122833 filed Oct. 9, 2021, which claims priority from Foreign Application No. PCT/CN2020/120154, filed Oct. 10, 2020. The priority applications are herein specifically incorporated by reference in their entirety.

FIELD

The present description relates to the production of 1,5-pentamethylene diisocyanate. More particularly, described herein is an improved phosgenation process for the production of 1,5-pentamethylene diisocyanate from a cadaverine salt in the presence of a tertiary amine that can be carried out at lower temperatures than those employed in conventional phosgenation reactions.

BACKGROUND

Isocyanates are typically produced from amines by phosgenation reactions via a carbamoyl chloride intermediate. In particular, 1,5-pentamethylene diisocyanate (PDI) is typically produced from the phosgenation of cadaverine and is an important building block for use in advanced coatings and in polyurethane production. For such applications, the purity of the PDI monomer is of great importance, as the presence of certain cyclic compounds greatly affect their downstream performance. Furthermore, due to the hazardous nature of phosgene and the noxious fumes associated with cadaverine, special facilities and precautions are necessary to produce PDI safely on an industrial scale. Thus, an improved process for producing PDI on an industrial scale that is less hazardous would be highly desirable.

SUMMARY

In a first aspect, described herein is a process for producing 1,5-pentamethylene diisocyanate (PDI) from a cadaverine salt, the process comprising: (a) providing a phosgene source; (b) providing a solution comprising a cadaverine salt dissolved in an inert solvent in the presence of a tertiary amine base; and (c) subjecting the solution to a liquid-phase phosgenation reaction to convert the cadaverine to PDI, the phosgenation reaction comprising a step of maintaining the reaction at a temperature range between 100° C. and 120° C. for a sufficient time to achieve a desired threshold yield of PDI, wherein the tertiary amine base is present in an amount sufficient to enable the phosgenation reaction to occur to completion at said temperature range.

In some embodiments, the phosgenation reaction in (c) is a multistage phosgenation reaction comprising at least a first stage in which the solution is heated to a first temperature such that the cadaverine reacts with phosgene from the phosgene source to produce a dicarbamoyl chloride intermediate, and a subsequent second stage in which the solution is further heated to a second temperature higher than the first temperature to subject the dicarbamoyl chloride intermediate to dehydrochlorination, wherein the second stage comprises the step of maintaining the reaction at temperatures between 100° C. and 120° C. for a sufficient time to achieve a threshold yield of PDI.

In some embodiments, the amounts of the phosgene source and/or tertiary amine base reactants employed in the multistage phosgenation reaction is lower than the amounts required to achieve the same PDI yield as a corresponding single-stage phosgenation reaction occurring only at the second temperature.

In some embodiments, the cadaverine salt (e.g., cadaverine dihydrochloride) is a bio-based cadaverine salt obtained from fermentation and/or enzymatic conversion, the enzymatic conversion preferably occurring via an immobilized whole (intact) cell biocatalyst to reduce cyclic compounds from cell lysis components. In some embodiments, the cadaverine salt provided is produced without distillation, or was not otherwise subjected to temperatures conducive to the formation of cyclic compounds.

In some embodiments, the tertiary amine base is a heterocyclic amine or a tertiary amine base having an sp2-hybridized N atom, such as pyridine; and the insert solvent is a solvent or solvent mixture having a boiling point of at least 120° C.

In further aspects, describe herein is a composition comprising having a content of THP or other cyclic compounds of below 0.1, 0.09, 0.08, 0.07, 0.06, 0.05, 0.04, 0.03, 0.02, or 0.01 wt %.

BRIEF DESCRIPTION OF THE DRAWINGS

In the appended drawings:

FIG. 1 shows the phosgenation reaction of cadaverine dihydrochloride to produce PDI.

DETAILED DESCRIPTION

General Definitions

Figure 2:
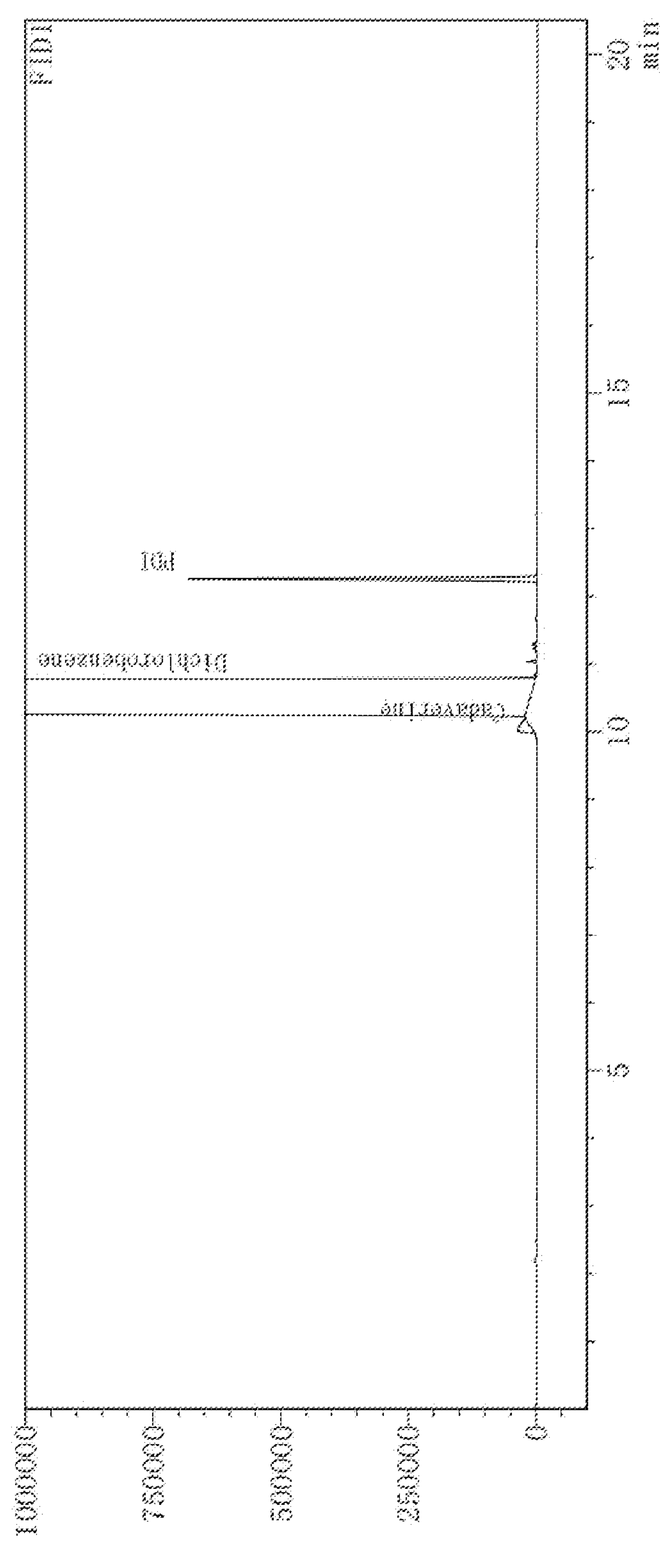
FIG. 2 shows a gas chromatograph from the PDI production process of Example 14.

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used herein, the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or process/method steps.

SEQUENCE LISTING

This application contains a Sequence Listing in computer readable form created Sep. 28, 2020 having a size of about 12 kb. The computer readable form is incorporated herein by reference.

| SEQ ID NO: | Description |
|---|---|
| 1 | 2-keto-acid decarboxylase wild-type nucleic acid sequence from *E. coli* strain BW25113 |
| 2 | 2-keto-acid decarboxylase wild-type amino acid sequence from *E. coli* strain BW25113 |

Industrial-scale production of 1,5-pentamethylene diisocyanate (PDI) from bio-based cadaverine (1,5-pentanediamine, pentamethylenediamine, PDA) using conventional processes is labor-intensive and requires high amounts of hazardous phosgene gas. As summarized in paragraphs [0003] and [0004] of European patent application No. 14908171.3 (published as EP 3235804), conventional industrial cadaverine production processes involve obtaining a solution of cadaverine salt by a fermentation or enzymatic conversion process, treating the salt solution with alkali, followed by extraction and evaporation and the like, which ultimately concludes in a distillation purification step to give cadaverine in its free base form. The cadaverine free base is then subjected to a conventional phosgenation reaction to obtain PDI. The conventional process is associated with the generation of noxious fumes from working with cadaverine in its free base form, utilizes relatively large amounts of hazardous phosgene gas, and requires high temperatures (e.g., above 170° C.) to obtain reasonable yields. The processes described herein relate to the production of PDI by liquid-phase phosgenation of a cadaverine salt solution in the presence of an amount of a tertiary amine base sufficient to allow the completion of the phosgenation reaction at temperatures substantially lower than those conventionally employed.

In a first aspect, described herein is a process for producing PDI from a cadaverine salt. The process generally comprises preparing a solution comprising a cadaverine salt dissolved in an inert solvent in the presence of a tertiary amine base. The solution is then subjected to a liquid-phase phosgenation to convert the cadaverine to PDI, with the phosgenation reaction comprising a step of maintaining the reaction at temperatures between 100° C. and 120° C. for a sufficient time to achieve a desired threshold yield of PDI. In addition to the facilitating the dissolution of the cadaverine salt in the inert solvent, the presence of the tertiary amine base in the liquid-phase phosgenation enables the phosgenation reaction to occur at a significantly lower temperature (e.g., 100 to 120° C.) than would otherwise be possible in the absence of the tertiary amine base.

In some embodiments, the phosgenation reaction temperatures in the processes described herein do not exceed about 119, 118, 117, 116, 115, 114, 113, 112, 111, or 110° C. Higher temperatures were not found to be beneficial in terms of PDI yield and/or purity, and were associated with a more rapid accumulation of an insoluble dark polymeric material in the reaction solution. Furthermore, the ability of carrying out the processes described herein at temperatures well below those employed in conventional phosgenation reactions results in considerable energy cost savings over time. In some embodiments, the phosgenation reaction temperatures in the processes described herein do not fall below 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. In some embodiments, lower temperatures were not beneficial to the processes described herein, for example in terms of initial dissolution of the reactants in the inert solvent and/or formation of mono- and/or dicarbamoyl chloride intermediates. In some embodiments, the phosgenation reaction in the processes described herein comprise a step of maintaining the reaction at temperatures between 100 and 115, 105 and 115, 110 and 115, or 100 and 110° C.; or at about 110° C. for a sufficient time to achieve a threshold yield of PDI. In some embodiments, the overall temperature range of the processes described herein may be from about 20 to 125, 20 to 120, 20 to 115, 25 to 115, 30 to 115, 35 to 115, 40 to 115, 45 to 115, or 50 to 115° C.

The phosgenation reactions described herein are preferably carried out at the shortest duration required to reach the desired PDI yield while maintaining an acceptable degree of purity. In some embodiments, phosgenation reactions described herein comprise a step of maintaining the reaction at temperatures between 100° C. and 120° C. for at least 1.5, 2, 2.5, or 3 hours. In some embodiments, phosgenation reaction described herein comprising a step of maintaining the reaction at temperatures between 100° C. and 120° C. for no more than 6, 7, 8, 9, 10, I1, or 12 hours. In some embodiments, phosgenation reaction described herein comprising a step of maintaining the reaction at temperatures between 100° C. and 120° C. for 1.5 to 6, 2 to 6, 2 to 5.5, 2.5 to 5.5, 2.5 to 6, or 3 to 5 hours.

In some embodiments, phosgenation reactions described herein employ a multistage phosgenation reaction comprising at least a first stage and a second stage. In the first stage, the reactants are heated to at a first temperature (or maintained in a first temperature range) enabling the cadaverine to react with phosgene from the phosgene source to produce a carbamoyl chloride intermediate (e.g., mono- and/or dicarbamoyl chloride intermediate). In the second stage, the reactants are further heated to a second temperature higher than the first temperature to subject the carbamoyl chloride intermediate to dehydrochlorination, thereby producing the PDI. For greater clarity, the second stage comprises the step described herein of maintaining the reaction at temperatures between 100° C. and 120° C. for a sufficient time to achieve a threshold yield of PDI. It was generally found that the multistage phosgenation reaction produced beneficial results in terms of PDI yield and/or purity, relative to a corresponding phosgenation reaction carried out at only a single higher temperature range (e.g., at only the second stage temperature). In some embodiments, the amounts of the phosgene source and/or tertiary amine base reactants employed in the multistage phosgenation reaction may be lower than the amounts required to achieve the same PDI yield as a corresponding single-stage phosgenation reaction occurring only at the second temperature. In some embodiments, the first temperature may be from about 30 to 65, 35 to 65, 35 to 60, 40 to 60, 35 to 55, 40 to 55, or 45 to 55° C. In some embodiments, the first temperature may be about 50° C. The reaction times employed during the first and second stages may be varied and/or optimized depending on particular reaction conditions in order to optimize for PDI yield and/or purity. In some embodiments, the first stage may comprise maintaining the solution at the first temperature for at least 0.5, 1, or 2 hours; or for 0.5 to 3, 0.5 to 2.5, 0.5 to 2, 1 to 2.5, or 1 to 2 hours. In some embodiments, the second stage may comprise maintaining the solution at the second temperature for at least 1.5, 2, 2.5, or 3 hours; or for 1.5 to 6, 2 to 6, 2 to 5.5, 2.5 to 5.5, 2.5 to 6, or 3 to 5 hours.

In some embodiments, phosgenation reactions described herein allow for a reduction in the amounts of reactants consumed over corresponding conventional processes. Such reductions greatly reduce operating costs. In some embodiments, phosgenation reactions described herein may employ 3 to 30, 4 to 29, 4 to 27, 4 to 24, 4 to 18, or 4.5 to 18 mols of phosgene per mole of cadaverine salt. While higher amounts or stoichiometric ratios of phosgene may be employed, minimal beneficial effect in terms of PDI yield and/or purity was observed by doing so. Furthermore, because of the toxic properties of phosgene, reducing the amounts of phosgene reactants in an industrial scale process is also advantageous in terms of safety and regulatory concerns. As used herein, the mols of phosgene refer to the number of mols of phosgene added to and/or consumed in the phosgenation reaction regardless of the source of the phosgene. For example, one mol of triphosgene is expected to be converted to three mols of phosgene during phosgenation reactions described herein. Thus, one mol of triphosgene as a phosgene source corresponds to three mols of phosgene in the stoichiometric values and ratios described herein.

Addition of a tertiary amine (e.g., pyridine or TMEDA) to the phosgenation reactions described herein, either undiluted or diluted with an inert solvent, lowered the temperatures required for PDI production. In some embodiments, phosgenation reactions described herein may employ a sufficient amount of a tertiary amine to enable the phosgenation reaction to occur to completion or near completion at the temperature range of 100 to 120° C. In some embodiments, phosgenation reactions described herein may employ at least 4, 4.5, 5, 5.5, or 6 mols of tertiary amine per mole of cadaverine salt. Higher amounts of tertiary amine base employed showed minimal benefit in terms of PDI yield and/or purity. Conversely, employing high excess of tertiary amine base (which would be cost prohibitive on an industrial scale) was found herein to be associated with a higher proportion of soluble by-products in the final reaction solution observable by GC analysis, thereby reducing overall purity of the PDI produced. In some embodiments, such soluble by-products may be difficult to remove by subsequent distillation if their boiling points are similar to that of PDI.

In some embodiments, the cadaverine salt employed in the phosgenation reactions described herein is preferably a bio-based cadaverine salt obtained from fermentation (e.g., of a microorganism engineered to produce cadaverine) and/or enzymatic conversion (e.g., from lysine or lysine-HCl salt, preferably a purified lysine-HCl salt). In some embodiments, the enzymatic conversion preferably occurs via an immobilized whole (intact) cell biocatalyst (e.g., whole cells expressing lysine decarboxylase) to reduce cyclic compounds from cell lysis components. In some embodiments, the cadaverine salt is cadaverine dihydrochloride. During the preparation of cadaverine by conventional processes, cyclic compounds containing an unsaturated bond, such as 2,3,4,5-tetrahydropyridine (THP or 1-piperidine), are also produced which must then be removed to not interfere with downstream polymerization applications (e.g., in nylon production) (EP 3235804). The PDI production processes described herein are at least in part motivated by the discovery herein that such cyclic compounds result from exposure of cadaverine to high temperatures, such as when cadaverine solutions are subjected to a distillation step. Thus, in some embodiments, the cadaverine salts utilized herein may be produced without a distillation step, or were not otherwise subjected to temperatures sufficiently high to be conducive to the formation of cyclic compounds (e.g., 2,3,4,5-tetrahydropyridine [THP]; piperidine; 2-(aminomethyl)-3,4,5,6-tetrahydropyridine; 1-piperidinecarbonyl chloride; or 1(2H)-pyridinecarbonylchloride). The presence of any cyclic compounds in the cadaverine salt reactants may be carried through the phosgenation reaction described herein and reduce the overall purity and/or performance of the PDI ultimately produced.

In some embodiments, the cyclic compounds and/or other ingredients described herein may comprise THP, piperidine, piperidine; 2-(aminomethyl)-3,4,5,6-tetrahydropyridine; 1-piperidinecarbonyl chloride; 1(2H)-pyridinecarbonylchloride, or polymeric (insoluble) ingredients that impart a darker color to the PDI produced. As used herein, the term "cyclic compounds" refers to any compound or material present in a raw material (e.g., cadaverine salt) and/or end product (e.g., PDI) that may have certain influence on the performance of the end product for its intended commercial purpose. For example, any ring-containing compound or material may have certain influence on the performance of PDI in polymerization reactions (e.g., in polyurethane production) is considered a cyclic compound. In some embodiments, the content of THP or other cyclic compounds in the cadaverine salt described herein may be below 0.1, 0.09, 0.08, 0.07, 0.06, 0.05, 0.04, 0.03, 0.02, or 0.01 wt %.

In some embodiments, the PDI produced by the phosgenation reactions described herein may have a content of THP or other cyclic compounds of below 0.1, 0.09, 0.08, 0.07, 0.06, 0.05, 0.04, 0.03, 0.02, or 0.01 wt % before being subject to one or more distillation purification steps. Reduced levels of cyclic compounds—particularly soluble cyclic compounds described herein having boiling points similar to PDI—may be more difficult to remove from the PDI reaction solution via distillation, or may require more than one distillation purification step. Thus, reducing the levels of cyclic compounds upstream of any PDI distillation purification step is advantageous.

In some embodiments, the phosgene source employed in the phosgenation reactions described herein may be phosgene gas or triphosgene. The former is advantageous for large, industrial-scale processes while the latter is advantageous for lab- or smaller-scale processes for practicality and safety reasons. In some embodiments, the phosgene source is triphosgene and the tertiary amine base is reacted with the triphosgene to release phosgene for the phosgenation reaction. In some embodiments, the phosgene source is triphosgene and the tertiary amine base serves to facilitate dissolution of the cadaverine salt, to react with the triphosgene to release phosgene, and to catalyze the subsequent phosgenation reaction at the phosgenation temperature range. In some embodiments, carrying out the phosgenation reactions described herein at temperatures below about 200° C. is advantageous, since phosgene has been reported to start to undergo some thermal degradation at this temperature, there requiring more reactant. In some embodiments, carrying out the phosgenation reactions described herein at temperatures below about 170° C. is advantageous, since triphosgene was reported to degrade that this temperature into a mixture of $CO_2$, phosgene, and carbon tetrachloride ($CCl_4$), thereby requiring more reactant (Cotarca et al., 2017).

In some embodiments, the tertiary amine base suitable for the phosgenation reactions described herein may be a heterocyclic amine or a tertiary amine base having an sp2-hybridized N atom. In some embodiments, the tertiary amine base may be pyridine, TMEDA, or mixture thereof. In some embodiments, the phosgenation reactions described herein may employ a hydrochloride salt of cadaverine, which produces a chloride salt of the tertiary amine base as a by-product. This tertiary amine hydrochloride salt (e.g., pyridine hydrochloride) may be isolated from the reaction solution and recycled.

In some embodiments, the inert solvent suitable for the phosgenation reactions described herein may comprise or consist of chlorobenzene, dichlorobenzene, toluene, nitrobenzene, or any mixture thereof. Other inert solvents conventionally used in phosgenation reactions may also be considered. In some embodiments, the insert solvent may be a solvent or solvent mixture having a boiling point of at least 120, 125, or 130° C.

In some embodiments, the desired threshold yield of PDI of the phosgenation reactions described herein may be at least 50, 55, 60, 65, 70, 75, or 80%.

In some aspects, described herein is a composition comprising the PDI produced by a process described herein having a content of THP or other cyclic compounds of below 0.1, 0.09, 0.08, 0.07, 0.06, 0.05, 0.04, 0.03, 0.02, or 0.01 wt %.

In some aspects, described herein is a composition comprising PDI in which the content of THP or other cyclic compounds in the PDI is below 0.1, 0.09, 0.08, 0.07, 0.06, 0.05, 0.04, 0.03, 0.02, or 0.01 wt %.

In some embodiments, the process described herein may take the form of a one-pot synthesis in which the cadaverine salt and phosgene source are slowly combined in the inert solvent in the presence of the tertiary amine base in a single vessel and subsequently heated to begin the phosgenation reaction.

In some embodiments, the PDI produced by the processes described herein may be subjected to a distillation purification step.

In some embodiments, the PDI produced by the process described herein may be used in (or may be of sufficient purity to be used in) various applications, such as in polyurethane production, coatings, resins, sealants, and in textiles.

EXAMPLES

Example 1: General Materials and Methods

The following reference materials are used in the Examples: Recombinant DNA manipulations generally follow methods described by Sambrook et al., 2001. Restriction enzymes, T4 DNA ligase, Rapid DNA Ligation Kit, SanPrep Column DNA Gel Extraction Kit, Plasmid Mini-Prep Kit and agarose are purchased from Sangon Biotech (Shanghai, China). TE buffer contains 10 mM Tris-HCl (pH 8.0) and 1 mM $Na_2EDTA$ (pH 8.0). TAE buffer contains 40 mM Tris-acetate (pH 8.0) and 2 mM $Na_2EDTA$.

In Example 2, restriction enzyme digests were performed in buffers provided by Sangon Biotech. A typical restriction enzyme digest contains 0.8 μg of DNA in 8 μL of TE, 2 μL of restriction enzyme buffer (10× concentration), 1 μL of bovine serum albumin (0.1 mg/mL), 1 μL of restriction enzyme and 8 μL TE. Reactions are incubated at 37° C. for 1 h and analyzed by agarose gel electrophoresis. The DNA used for cloning experiments was digested and the reaction was terminated by heating at 70° C. for 15 min followed by extraction of the DNA using SanPrep Column DNA Gel Extraction Kit. The concentration of DNA in the sample was determined as follows. An aliquot (10 μL) of DNA was diluted to 1 mL in TE and the absorbance at 260 nm was measured relative to the absorbance of TE. The DNA concentration was calculated based on the fact that the absorbance at 260 nm of 50 μg/mL of double stranded DNA is 1.0.

Agarose gel typically contains 0.7% agarose (w/v) in TAE buffer. Ethidium bromide (0.5 μg/ml) is added to the agarose to allow visualization of DNA fragments under a UV lamp. Agarose gels were run in TAE buffer. The size of the DNA fragments was determined using two sets of 1 kb Plus DNA Ladder obtained from Sangon Biotech.

Example 2: Cloning, Expression and Activity Testing of Lysine Decarboxylase Expressed in *E. coli*

An *Escherichia coli* lysine decarboxylase kdc (2-keto-acid decarboxylase) gene was synthesized and cloned into pET21a (Millipore Sigma, formerly Novagen). The wild-type kdc nucleic acid sequence from *E. coli* strain BW25113 (E.C. 4.1.1.18) is represented by SEQ ID NO: 1, and amino acid sequence by SEQ ID NO: 2, annotated as lysine decarboxylase.

Plasmid containing the kdc gene was transformed into BL21(DE3) *E. coli* cells. Empty plasmid pET21a was also transformed as a negative control. For enzyme expression and characterization experiments, flasks containing 40 mL TB were inoculated at 5% from overnight cultures and shaken. Flasks were incubated at 30° C. at 250 rpm shaking for 2 hours, then protein production was induced with 0.2 mM Isopropyl β-D-1-thiogalactopyranoside (IPTG) and incubated for 4 more hours at 30° C. while shaking. Cells were harvested by centrifugation and pellets were stored at −80° C.

KDC enzymatic activity was assessed with a pH-based in vitro assay. The enzyme activity was tested using a commercial lysine-HCl salt. Unless otherwise specified, all chemicals were purchased from Sigma-Aldrich Chemical Company (St. Louis, MO, USA). First, cells were lysed using a benchtop sonicator according to the manufacturer's instructions. The cell lysates were partially clarified by centrifugation (14,000 g for 5 minutes). Protein concentrations of the resulting clarified lysates were measured via Bradford Protein Assay Kit (Sangon Biotech) according to the manufacturer's instructions. Lysates were normalized by protein concentration by dilution in 10 mM Tris buffer. The normalized lysates were then diluted 1:5 in 10 mM Tris buffer. 20 μL of lysate was added to each well for the multiple well plate assay. Each condition was performed in triplicate.

The reaction mixture contained 15% lysine-HCl, 0.04% pyridoxal-5'-phosphate (PLP). The pH of each reaction mixture was adjusted to approximately pH 6.5 by the addition of 1M $H_2SO_4$ and 1N NaOH. Lysate was then added to the reaction mixture while constantly maintaining the pH at 6.5 by the addition of 1M $H_2SO_4$. The amount of $H_2SO_4$ used was recorded and used to calculate activities of the enzyme. The assay reaction was completed when the addition of $H_2SO_4$ was no longer required to maintain pH at 6.5.

Example 3: Fermentation of Transformed *E. coli* Overexpressing KDC

For the present Example, the growth medium was prepared as follows: All solutions were prepared in distilled, deionized water. LB medium (1 L) contained Bacto™ tryptone (i.e., enzymatic digest of casein) (10 g), Bacto™ yeast extract (i.e., water-soluble portion of autolyzed yeast cell) (5 g), and NaCl (10 g). LB-glucose medium contains glucose (10 g). $MgSO_4$ (0.12 g), and thiamine hydrochloride (0.001 g) in 1 L of LB medium. LB-freeze buffer contained $K_2HPO_4$ (6.3 g). $KH_2PO_4$ (1.8 g), $MgSO_4$ (1.0 g), $(NH_4)_2SO_4$ (0.9 g), sodium citrate dihydrate (0.5 g) and glycerol (44 mL) in 1 L of LB medium. M9 salts (I L) contains $Na_2HPO_4$ (6 g), $KH_2PO_4$ (3 g), $NH_4Cl$ (1 g), and NaCl (0.5 g). M9 minimal medium contained D-glucose (10 g), $MgSO_4$ (0.12 g), and thiamine hydrochloride (0.001 g) in 1 L of M9 salts. Antibiotics were added where appropriate to the following final concentrations: ampicillin (Ap), 50 μg/mL; chloramphenicol (Cm), 20 μg/mL; kanamycin (Kan), 50 μg/mL; tetracycline (Tc), 12.5 μg/mL. Stock solutions of antibiotics were prepared in water with the exceptions of chloramphenicol, which was prepared in 95% ethanol and tetracycline, which was prepared in 50% aqueous ethanol. Aqueous stock solutions of IPTG were prepared at various concentrations.

The standard fermentation medium (1 L) contained $K_2HPO_4$ (7.5 g), ammonium iron (III) citrate (0.3 g), citric acid monohydrate (2.1 g), and concentrated $H_2SO_4$ (1.2 mL). Fermentation medium was adjusted to pH 7.0 by the addition of concentrated $NH_4OH$ before autoclaving. The following supplements were added immediately prior to initiation of the fermentation: D-glucose, $MgSO_4$ (0.24 g), potassium and trace minerals including $(NH_4)_6(Mo_7O_{24})\cdot 4H_2O$ (0.0037 g), $ZnSO_4\cdot 7H_2O$ (0.0029 g), $H_3BO_3$ (0.0247 g), $CuSO_4\cdot 5H_2O$ (0.0025 g), and $MnCl_2\cdot 4H_2O$ (0.0158 g). IPTG stock solution was added as necessary (e.g., when optical density at 600 nm lied between 15-20) to the indicated final concentration. Glucose feed solution and $MgSO_4$ (1M) solution were autoclaved separately. Glucose feed solution (650 g/L) was prepared by combining 300 g of glucose and 280 mL of $H_2O$. Solutions of trace minerals and IPTG were sterilized through 0.22-μm membranes. Antifoam (Sigma 204) was added to the fermentation broth as needed. Typical wet *E. coli* cell density reached 120 g/L.

Example 4: Conversion of Lysine Hydrochloride to PDA Hydrochloride Using Whole Cells Expressing Lysine Decarboxylase For the production of pentamethylenediamine (PDA)-HCl, 2 g of lysine decarboxylase-containing wet engineered *E. coli* was added to 1 L of a 200 g/L lysine hydrochloride solution containing 0.1 g/L PLP. pH was maintained at 6.5 using HCl. The temperature of the solution was brought to 37'C. Reaction was then started and lasted for 10 hours, while maintaining the pH at 6.5. Lysine content was determined by high performance liquid chromatography (HPLC) at the end of the reaction (<0.5% w/v).

The reaction mixture was passed through a 0.2-micron microfiltration membrane (to remove large particulates such as cells, bacterial fragments and aggregates) and a 10 kDa ultrafiltration membrane (to remove proteins and other soluble macromolecules in culture medium). The filtrate was concentrated to ¼ of the original volume under reduced pressure. A 2× volume of methanol was added to the mixture, and subsequently crystallized at 15° C. The solid was then collected and dried. This white solid product weighed at 174.67 g and was analyzed for PDA-HCl content. PDA-HCl content was found to be 99.3%, with a yield of 91.1%. The PDA-HCl salt was not subjected to a further distillation purification step.

Example 5: Conversion of Lysine Hydrochloride to PDA Hydrochloride Using Lysine Decarboxylase from Cell Lysates The same method was used for the production of PDA hydrochloride (PDA-HCl) as in Example 4, however, 2 g of lysates from lysine decarboxylase-containing engineered *E. coli* cells were added instead of whole cells. For obtaining soluble cell extracts, 2 g of *E. coli* engineered bacterial cells was added to 10 mL of a phosphate buffer solution (pH 7.0) and stirred well. The cells were then crushed by high-pressure homogenization and then centrifuged to obtain soluble cell extracts. The remaining white solid from the reaction weighed at 172.9 g. PDA-HCl content was found to be 99.5%, with a yield of 90.2%. The PDA-HCl salt was not subjected to a further distillation purification step.

Example 6: PDA Hydrochloride Crystallization with Ethanol

The same method was used for the production of PDA-HCl as in Example 4, however, ethanol was added instead of methanol for crystallization at 15° C. The remaining white solid from the reaction weighed at 177.35 g. PDA-HCl content was found to be 99.2%, with a yield of 92.5%. The PDA-HCl salt was not subjected to a further distillation purification step.

Example 7: PDA Hydrochloride Crystallization with Isopropanol

The same method was used for the production of PDA-HCl as in Example 4, however, 3 times the volume of isopropyl alcohol was added instead of methanol for crystallization at 15° C. The remaining white solid from the reaction weighed at 171.2 g. PDA-HCl content was found to be 99.4%, with a yield of 89.3%. The PDA-HCl salt was not subjected to a further distillation purification step.

Example 8: Increased Lysine Hydrochloride Concentration and Adjusted pH to 7

The same method was used for the production of PDA-HCl as in Example 4, however, the lysine hydrochloride concentration was at 300 g/L with a pH maintained at 7 instead of 200 g/L at a pH of 6.5, 4 g of engineered wet E coil was added instead of 2 g, 0.15 g/L of PLP instead of 0.1 g/L, and the reaction time was 13 hours instead of 10 hours. The remaining white solid from the reaction weighed at 223.4 g. PDA-HCl content was found to be 99.3%, with a yield of 91.5%. The PDA-HCl salt was not subjected to a further distillation purification step.

Example 12: Diisocyanate Analysis by Gas Chromatography

Subsequent examples generally relate to the production of a diisocyanate (1,5-pentamethylene diisocyanate [PDI])

from a diamine free base (PDA; Example 13) or a diamine salt (PDA-HCl; Examples 14-46). Where indicated, the PDI produced in subsequent examples was analyzed with a gas chromatograph with the following settings/parameters: Column: DB-5 30 m*0.25 mm*0.25 μm, inlet temperature: 160° C., Detector: detector temperature 280°, carrier gas flow rate: 2 mL/min, split ratio: 36:1, column oven: The initial temperature is 40° C., hold for 5 min, increase to 250° C. at 20° C./min, and hold for 5 min. Injection volume: 1 μL.

Example 13: PDI Production from PDA Free Base at Temperature Up to 170° C.

87.5 g (0.5 mol) of PDA-HCl salt was mixed with 200 g (1 mol) of 20% sodium hydroxide solution, stirred at room temperature for 1 h, and then dissolved in about 100 g of water under reduced pressure. After that, 200 g of ethanol was added at 20° C. and stirred until the solids were completely precipitated. After filtration, the mother liquor was desolvated under reduced pressure, and dried under a high vacuum of 1,000 Pa to obtain 51 g of PDA free base.

51 g (0.5 mol; 1 eq) of PDA free base and 1050 g of dichlorobenzene were mixed in a 2 L three-necked flask, heated to 60° C., and started to phosgene. The aeration rate was 2.5 g/min, and the tail gas was absorbed with 10% sodium hydroxide solution. After 40 min, the temperature was raised to 80° C., and the aeration rate was not changed. After 1 hour, the temperature was increased to 170° C. After 12 hours of aeration, a total of 2,050 g (20.7 mol; 41.4 eq) of phosgene was introduced, and samples were taken. The reaction yield was calculated by GC normalization method to 72.2%.

Following transfer to a rectification device, solvent dichlorobenzene was then removed at a pressure of 200 Pa at 46° C., and the temperature was raised to 65-66° C. to collect 49 g of a colorless liquid that was pentamethylene diisocyanate (PDI) with a yield of 63.6% and a GC purity of 99.5%:

$^{1}$H-NMR ($CDCl_3$, 400 MHz) δ: 3.32~3.35 (t, 4H, OCN—$CH_2$—H), 1.62~1.67 (m, 4H), 1.45~4.51 (m, 2H)

$^{13}$C NMR (400 MHz, $CDCl_3$) δ: 23.68, 30.63, 42.81, 122.06

Elemental Analysis: Theoretical C, 54.54; H, 6.54; N, 18.17; Measured C, 54.55: H, 6.48: N, 18.42.

PDI Production from PDA-HCl Salt

Figure 1:
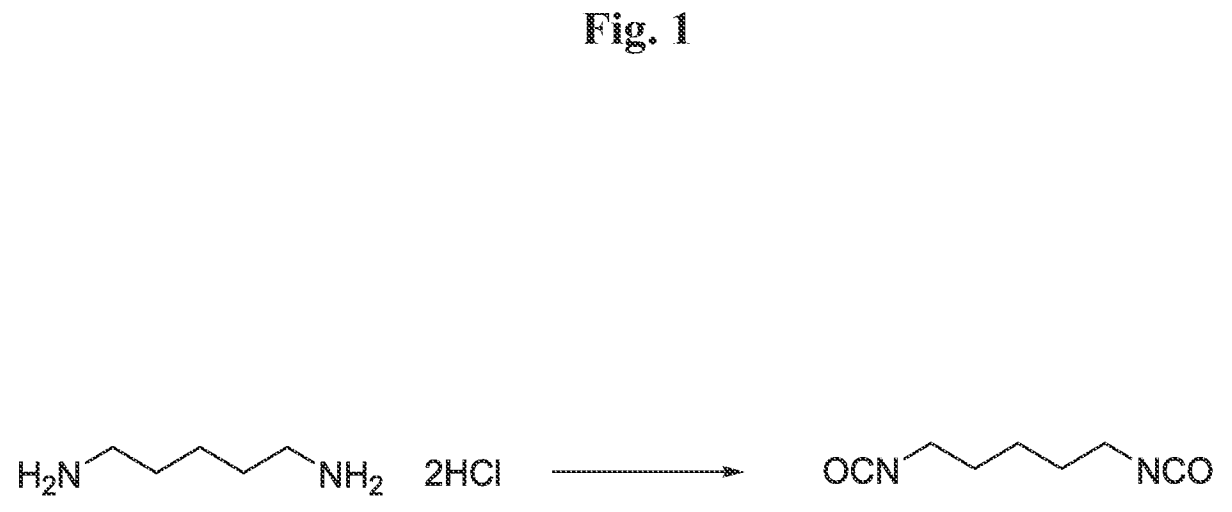

While Example 13 described a method for the production PDI from PDA free base, subsequent Examples relate to the production PDI from PDA-HCl salt (FIG. 1) through phosgenation reactions. More specifically, Examples 14-37 and FIGS. 2 and 3 as well as Table 1 relate to the production of PDI from PDA-HCl using phosgene gas directly as a phosgene source. For reasons of safety and practicality, further experiments were performed using triphosgene instead of phosgene. Thus, Examples 38-46, FIGS. 4-7 and Table 2 relate to the production of PDI from PDA-HCl using triphosgene as an indirect phosgene source. Nevertheless, it is expected that results obtained with triphosgene are applicable to phosgene (and vice versa), given that one mol of triphosgene is expected to be converted to three mols of phosgene during phosgenation reactions described herein. Tables 1 and 2 provide summary tables facilitating comparison between the reaction conditions in Examples 14-46, and Example 47 provides an overview of the results.

TABLE 1

Figure 3:
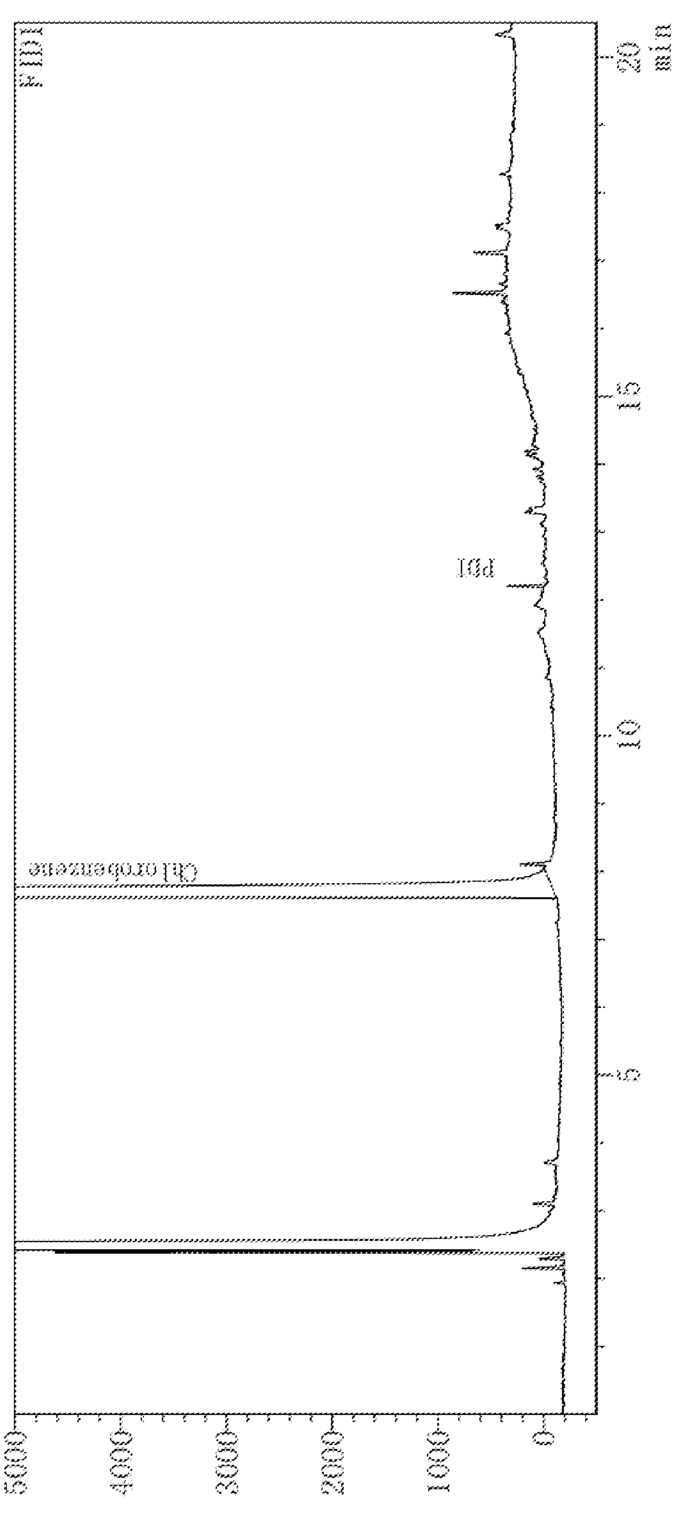
FIG. 3 shows a gas chromatograph from the PDT production process of Example 16.

| Example | PDA-HCl | Phosgene | Tertiary amine | Inert solvent(s) | Phosgenation temperature | Yield | GC trace | Overall purity |
|---|---|---|---|---|---|---|---|---|
| 14 | 1 eq | 41.4 eq | — | dichlorobenzene | (1) 60° C. for 40 min<br>(2) 80° C. for 1 h<br>(3) 170° C. for 12 h | 88.1% | FIG. 2 | +++++<br>** |
| 15 | 1 eq | 41.4 eq | — | nitrobenzene | (1) 60° C. for 40 min<br>(2) 80° C. for 1 h<br>(3) 130° C. for 1 h<br>(4) 210° C. for 11 h | 56.2% | — | +++<br>** |
| 16 | 1 eq | 20.2 eq | — | chlorobenzene | (1) 60° C. for 40 min<br>(2) 80° C. for 1 h<br>(3) 130° C. for 5 h | 2.4% | FIG. 3 | Clear |
| 17 | 1 eq | 20.2 eq | — | chlorobenzene | (1) 60° C. for 40 min<br>(2) 80° C. for 1 h<br>(3) 130° C. for 5 h | 3.0% | — | Clear |
| 18 | 1 eq | 41.4 eq | — | chlorobenzene | (1) 60° C. for 40 min<br>(2) 80° C. for 1 h<br>(3) 130° C. for 12 h | 9.4% | — | Clear |
| 19 | 1 eq | 20.2 eq | — | chlorobenzene + aniline | (1) 60° C. for 40 min<br>(2) 80° C. for 1 h<br>(3) 130° C. for 5 h | 3.8% | — | Clear |
| 20 | 1 eq | 24.2 eq | TMEDA (15.1 eq) | — | (1) 100° C. for 16,7 h | 36.1% | — | ++<br>**** |
| 21 | 1 eq | 24.2 eq | pyridine (22.1 eq) | — | (1) 100° C. for 16.7 h | 43.1% | — | +++<br>**** |
| 22 | 1 eq | 24.2 eq | TMEDA (2 eq) | chlorobenzene | (1) 100° C. for 16.7 h | 37.6% | — | ++<br>** |
| 23 | 1 eq | 24.2 eq | TMEDA (2 eq) | toluene | (1) 100° C. for 16.7 h | 15.2% | — | +<br>*** |
| 24 | 1 eq | 24.2 eq | pyridine (2 eg) | chlorobenzene | (1) 100° C. for 16.7 h | 44.2% | — | +++<br>*** |
| 25 | 1 eq | 24.2 eq | pyridine (2 eq) | toluene | (1) 100° C. for 16.7 h | 20.3% | — | +<br>*** |
| 26 | 1 eq | 24.2 eq | TMEDA (15.1 eg) | — | (1) 80° C. for 16.7 h | 16.3% | — | +<br>** |
| 27 | 1 eq | 24.2 eq | pyridine (22.1 eg) | — | (1) 80° C. for 16.7 h | 22.3% | — | +<br>** |

TABLE 1-continued

| Example | PDA-HCl | Phosgene | Tertiary amine | Inert solvent(s) | Phosgenation temperature | Yield | GC trace | Overall purity |
|---|---|---|---|---|---|---|---|---|
| 28 | 1 eq | 24.2 eq | TMEDA (2 eq) | chlorobenzene | (1) 80° C. for 16.7 h | 16.5% | — | + * |
| 29 | 1 eq | 24.2 eq | TMEDA (2 eq) | toluene | (1) 80° C. for 16.7 h | 8.2% | — | Clear |
| 30 | 1 eq | 24.2 eq | pyridine (2 eq) | chlorobenzene | (1) 80° C. for 16.7 h | 21.9% | — | + * |
| 31 | 1 eq | 24.2 eq | pyridine (2 eq) | toluene | (1) 80° C. for 16.7 h | 9.9% | — | Clear |
| 32 | 1 eq | 24.2 eq | TMEDA (15.1 eg) | — | (1) 50° C. for 4 h (2) 80° C. for 12.7 h | 16.4% | — | + ** |
| 33 | 1 eq | 24.2 eq | pyridine (22.1 eq) | — | (1) 50° C. for 4 h (2) 80° C. for 12.7 h | 21.5% | — | + ** |
| 34 | 1 eq | 24.2 eq | TMEDA (2 eq) | chlorobenzene | (1) 50° C. for 4 h (2) 80° C. for 12.7 h | 17.1% | — | + * |
| 35 | 1 eq | 24.2 eq | TMEDA (2 eq) | toluene | (1) 50° C. for 4 h (2) 80° C. for 12.7 h | 7.9% | — | Clear |
| 36 | 1 eq | 24.2 eq | pyridine (2 eq) | chlorobenzene | (1) 50° C. for 4 h (2) 80° C. for 12.7 h | 22.3% | — | + * |
| 37 | 1 eq | 24.2 eq | pyridine (2 eq) | toluene | (1) 50° C. for 4 h (2) 80° C. for 12.7 h | 8.6% | — | Clear |

† Overall purity of the crude reaction solution; **** to * Most to least amount of insoluble dark polymeric material found at bottom of flask; +++++ to +: Highest to lowest purity of reaction solution by gas chromatography; "Clear": No insoluble dark polymeric material found at bottom of flask, but yield below 10%.

TABLE 2

Figure 4:
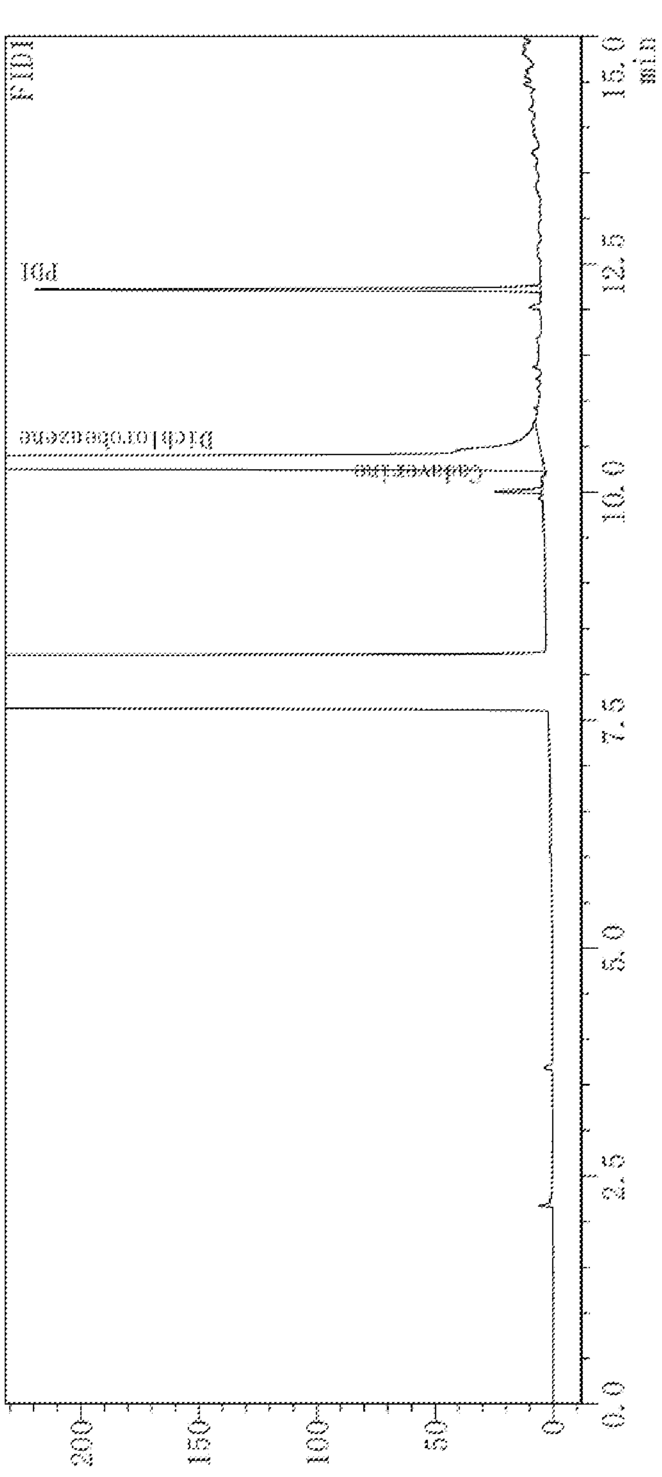
FIG. 4 shows a gas chromatograph from the PDI production process of Example 38.
Figure 5:
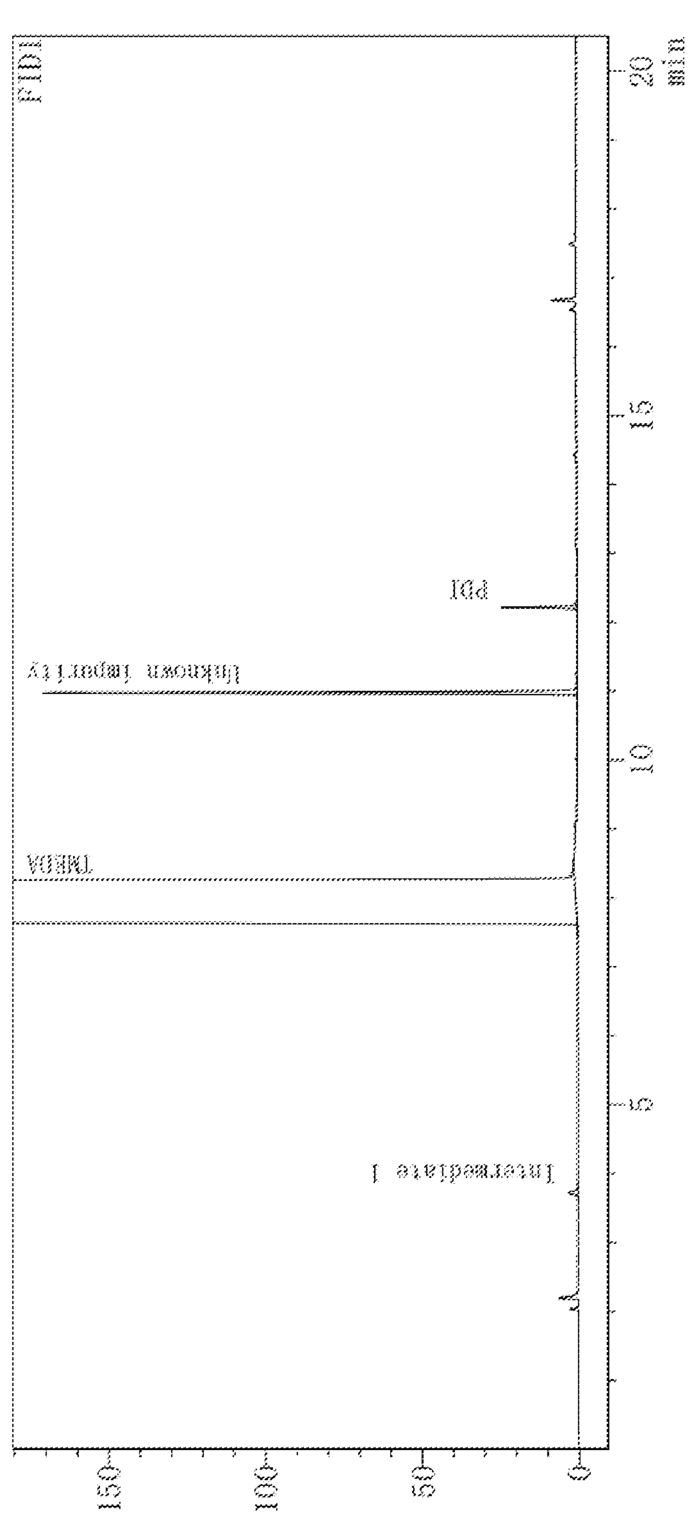
FIG. 5 shows a gas chromatograph from the PDI production process of Example 39.
Figure 6:
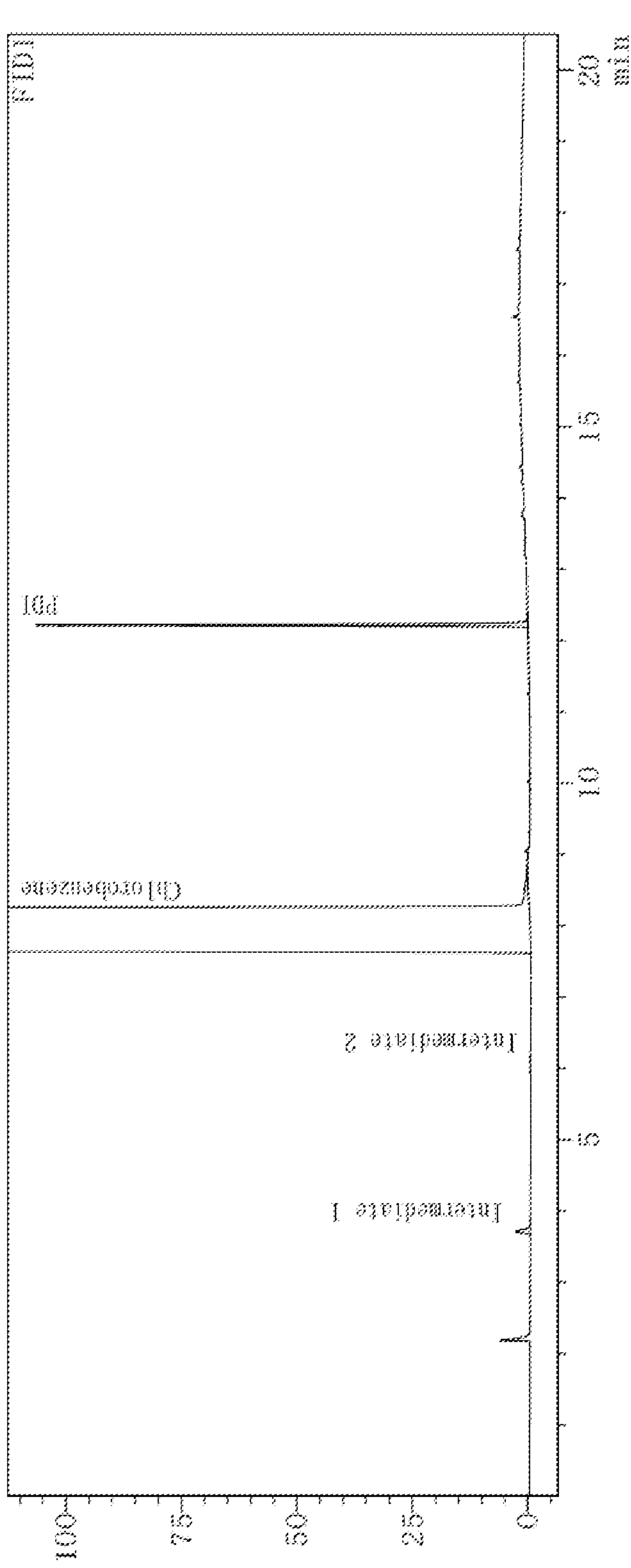
FIG. 6 shows a gas chromatograph from the PDI production process of Example 41.
Figure 7:
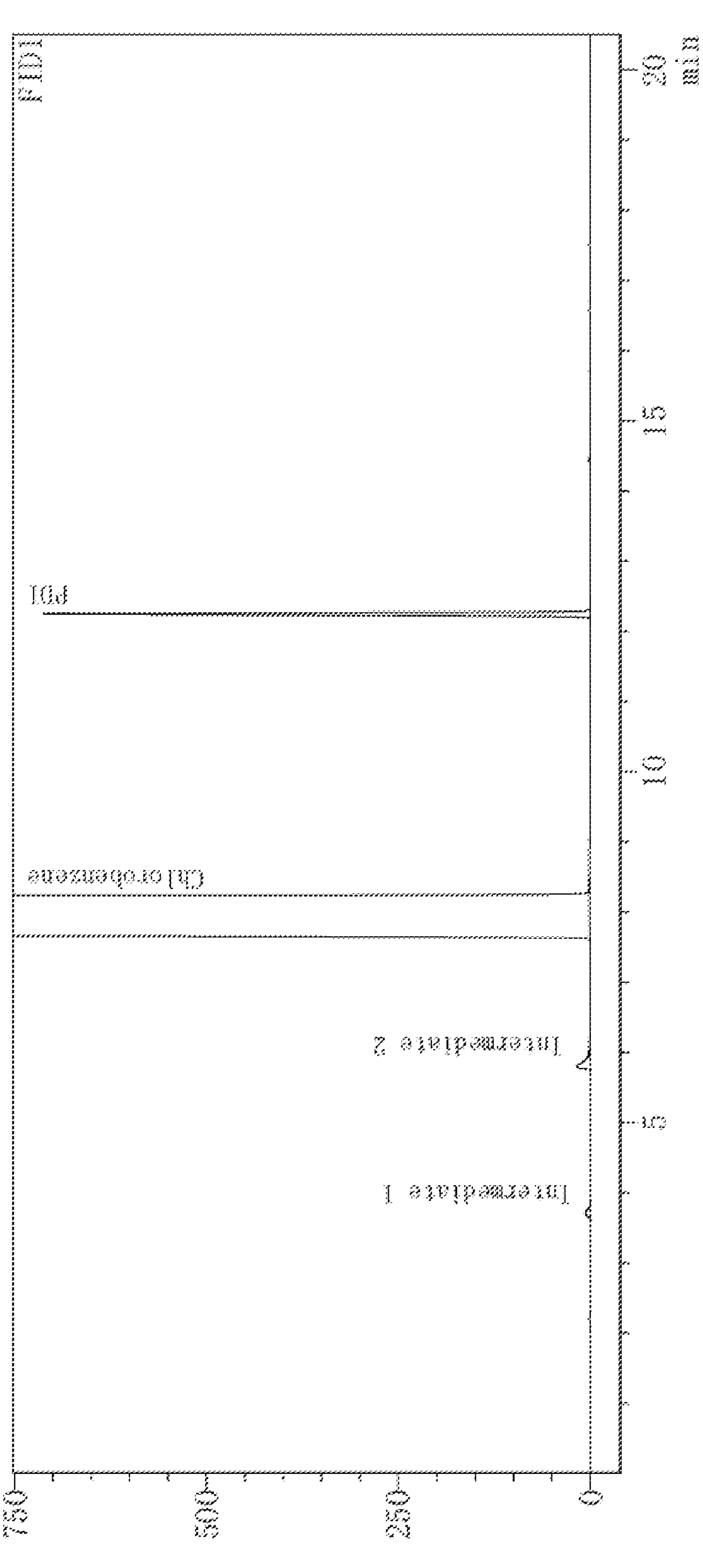
FIG. 7 shows a gas chromatograph from the PDI production process of Example 44.

| Example | PDA-HCl | Triphosgene (phosgene) | Tertiary amine | Solvent(s) | Phosgenation temperature | Yield | GC trace | Overall purity |
|---|---|---|---|---|---|---|---|---|
| 38 | 1 eq | 20.2 eq (60.6 eg) | — | dichlorobenzene | (1) 170° C. for 6 h | 68% | FIG. 4 | ++++ ** |
| 39 | 1 eq | 10 eg (30 eq) | TMEDA (17.1 eq) | chlorobenzene/ dichlorobenzene | (1) 100° C. until completion | 15.2% | FIG. 5 | + ** |
| 40 | 1 eq | 10 eq (30 eg) | TMEDA (2 eq) | chlorobenzene/ dichlorobenzene | (1) 100° C. until completion | 16.3% | — | + ** |
| 41 | 1 eg | 10 eq (30 eg) | pyridine (4 eq) | chlorobenzene/ dichlorobenzene | (1) 100° C. until completion | 31.4% | FIG. 6 | ++ * |
| 42 | 1 eq | 10 eq (30 eg) | pyridine (24 eq) | chlorobenzene | (1) 100° C. until completion | 55.6% | — | +++ * |
| 43 | 1 eq | 10 eg (30 eq) | pyridine (4 eq) | chlorobenzene/ dichlorobenzene | (1) 80° C. until completion | 20.3% | — | + * |
| 44 | 1 eq | 5 eq (15 eq) | pyridine (2 eq) | chlorobenzene | (1) 50° C. for 1 h (2) 80° C. for 3 h | 20.9% | FIG. 7 | + * |
| 45 | 1 eq | 1.5 eq (4.5 eq) | pyridine (2 eq) | chlorobenzene | (1) 50° C. for 1 h (2) 80° C. for 3 h (3) 110° C. for 3 h (4) 120° C. for 3 h | (1) 0% (2) 12.1% (3) 22.6% (4) 22.7% | — | + * |
| 46 | 1 eq | 1.5 eq (4.5 eq) | pyridine (6 eq) | chlorobenzene | (1) 50° C. for 1 h (2) 80° C. for 3 h (3) 110° C. for 3 h (4) 120° C. for 3 h | (1) 0% (2) 18.1% (3) 80.2% (4) 80.2% | — | +++++ * |

†: Overall purity of the crude reaction solution; **** to * Most to least amount of insoluble dark polymeric material found at bottom of flask; +++++ to +: Highest to lowest purity of reaction solution by gas chromatography; "Clear": No insoluble dark polymeric material found at bottom of flask, but yield below 10%.

Example 14: PDI Production from PDA-HCl with Phosgene at Temperatures Up to 170° C.

87.5 g (0.5 mol) of PDA-HCl and 1050 g of dichlorobenzene were mixed in a 2 L three-necked flask, heated to 60° C., started phosgenation at rate of 2.5 g/min, and the tail gas was quenched with 10% sodium hydroxide solution. After 40 min, the temperature was raised to 80 TC. After 1 h, the temperature was increased to 170° C. and allowed to react for another 12 hours. A total of 2,050 g (20.7 mol) of phosgene was introduced and samples were taken. The reaction yield was 88.1%. Gas chromatography results are shown in FIG. 2.

Example 15: PDI Production from PDA-HCl with Phosgene at Temperatures Up to 210° C.

87.5 g (0.5 mol) of PDA-HCl and 1050 g of nitrobenzene were mixed in a 2 L three-necked flask, heated to 60° C., started phosgenation at rate of 2.5 g/min, and the tail gas was quenched with 10% sodium hydroxide solution. After 40 min, the temperature was increased to 80° C. After 1 h, the temperature was increased to 130° C., and the ventilation speed was not changed. After 1 h, the temperature was increased to 210° C., and allowed to react for another 11 h. A total of 2.050 g (20.7 mol) of phosgene was passed in. The reaction yield was 56.2%, but relatively high amount of insoluble dark polymeric material was found at the bottom of the flask.

Example 16: PDI Production from PDA-HCl with Phosgene at Temperatures Up to 130° C.

87.5 g (0.5 mol) of PDA-HCl and 612.5 g of chlorobenzene were mixed in a 2 L three-necked flask, heated to 60° C., started phosgenation at rate of 2.5 g/min, and the tail gas was quenched with a 10% sodium hydroxide solution. After 40 min, the temperature was raised to 80° C. After 1 h, the temperature was increased to 130° C. and allowed to react for another 5 h. A total of 1,000 g (10.1 mol) of phosgene was introduced and samples were taken. The reaction yield was 2.4%. Gas chromatography results are shown in FIG. 3.

Example 17: PDI Production from PDA-HCl with Phosgene at Temperatures Up to 130° C.

87.5 g (0.5 mol) of PDA-HCl and 1050 g of chlorobenzene were mixed in a 2 L three-necked flask, heated to 60° C., started phosgenation at rate of 2.5 g/min, and the tail gas was quenched with 10% sodium hydroxide solution. After 40 min, the temperature was increased to 80° C. After 1 h, the temperature was increased to 130° C., and allowed to react for another 5 h. A total of 1,000 g (10.1 mol) of phosgene was introduced and samples were taken. The reaction yield was 3.0%.

Example 18: PDI Production from PDA-HCl with Phosgene at Temperatures Up to 130° C.

87.5 g (0.5 mol) of PDA-HCl and 1050 g of chlorobenzene were mixed in a 2 L three-necked bottle, heated to 60° C., started phosgenation at rate of 2.5 g/min, and the tail gas was quenched with 10% sodium hydroxide solution. After 40 min, the temperature was increased to 80° C. After 1 hour, the temperature was increased to 130° C., and allowed to react for another 12 h. A total of 2,050 g (20.7 mol) of phosgene was introduced and sampled. The reaction yield was 9.4%.

Example 19: PDI Production from PDA-HCl with Phosgene at Temperatures Up to 130° C. in the Presence of Aniline 87.5 g (0.5 mol) of PDA-HCl and 612.5 g of chlorobenzene were mixed in a 2 L three-necked flask, aniline (6 mL) was added as a catalyst, and the mixture was heated to 60° C. to begin phosgenation at rate of 2.5 g/min. The tail gas was quenched with 10% sodium hydroxide solution. After 40 min, the temperature was raised to 80° C. After 1 h. the temperature was increased to 130° C. and allowed to react for another 5 h. A total of 1,000 g (10.1 mol) of phosgene was introduced. Samples were taken and the reaction yield was 3.8%.

Example 20: PDI Production from PDA-HCl with Phosgene at 100° C. with TMEDA as Solvent In a 2 L three-necked flask, a solution of 87.5 g (0.5 mol) PDA-HCl and 875 g TMEDA was heated to 100° C. and phosgenation was started at 1.2 g phosgene per min. The tail gas was quenched with 10% sodium hydroxide solution. After 1,000 min, phosgenation reaction ended and the mixture was cooled to 25° C. A total of 1,200 g (12.1 mol) phosgene was introduced and samples were taken. The reaction yield was 36.1%, but relatively high amount of insoluble dark polymeric material was found at the bottom of the flask.

Example 21: PDI Production from PDA-HCl with Phosgene at 100° C. with Pyridine as Solvent In a 2 L three-necked flask, a solution of 87.5 g (0.5 mol) PDA-HCl and 875 g pyridine was heated to 100° C. and phosgenation was started at 1.2 g phosgene per min. The tail gas was quenched with 10% sodium hydroxide solution. After 1,000 min, phosgenation reaction ended and the mixture was cooled to 25° C. A total of 1,200 g (12.1 mol) phosgene was introduced and samples were taken. The reaction yield was 43.1%, but relatively high amount of insoluble dark polymeric material was found at the bottom of the flask.

Example 22: PDI Production from PDA-HCl with Phosgene at 100° C. with TMEDA/Chlorobenzene as Solvent In a 2 L three-necked flask, a solution of 87.5 g (0.5 mol) PDA-HCl, 1,050 g chlorobenzene and 116 g (1 mol) TMEDA was heated to 100° C. and phosgenation was started at 1.2 g phosgene per min. The tail gas was quenched with 10% sodium hydroxide solution. After 1,000 min. phosgenation reaction ended and the mixture was cooled to 25° C. A total of 1,200 g (12.1 mol) phosgene was introduced and samples were taken. The reaction yield was 37.6%.

Example 23: PDI Production from PDA-HCl with Phosgene at 100° C. with TMEDA/Toluene as Solvent In a 2 L three-necked flask, a solution of 87.5 g (0.5 mol) PDA-HCl, 1,050 g toluene and 116 g (I mol) TMEDA was heated to 100° C. and phosgenation was started at 1.2 g phosgene per min. The tail gas was quenched with 10% sodium hydroxide solution. After 1,000 min, phosgenation reaction ended and the mixture was cooled to 25° C. A total of 1,200 g (12.1 mol) phosgene was introduced and samples were taken. The reaction yield was 15.2%, but relatively high amount of insoluble dark polymeric material was found at the bottom of the flask.

Example 24: PDI Production from PDA-HCl with Phosgene at 100° C. with Pyridine/Chlorobenzene as Solvent In a 2 L three-necked flask, a solution of 87.5 g (0.5 mol) PDA-HCl, 1,050 g chlorobenzene and 79 g (1 mol) pyridine was heated to 100° C. and phosgenation was started at 1.2 g phosgene per min. The tail gas was quenched with 10% sodium hydroxide solution. After 1,000 min, phosgenation reaction ended, and the mixture was cooled to 25° C. A total of 1,200 g (12.1 mol) of phosgene was introduced and samples were taken. The reaction yield was 44.2%, but relatively high amount of insoluble dark polymeric material was found at the bottom of the flask.

Example 25: PDI Production from PDA-HCl with Phosgene at 100° C. with Pyridine/Toluene as Solvent In a 2 L three-necked flask, a solution of 87.5 g (0.5 mol) PDA-HCl, 1,050 g toluene and 79 g (1 mol) pyridine was heated to 100° C. and phosgenation is started at 1.2 g phosgene per min. The tail gas was quenched with 10% sodium hydroxide solution. After 1,000 minutes, phosgenation reaction ended, and the mixture was cooled to 25° C. A total of 1,200 g (12.1 mol) phosgene was introduced and samples were taken. The reaction yield was 20.3%, but relatively high amount of insoluble dark polymeric material was found at the bottom of the flask.

Example 26: PDI Production from PDA-HCl with Phosgene at 80° C. with TMEDA as Solvent The phosgenation reaction was performed as described in Example 20 except that the temperature was heated to 80° C. instead of 100° C. The reaction yield was 16.3%.

Example 27: PDI Production from PDA-HCl with Phosgene at 80° C. with Pyridine as Solvent The phosgenation reaction was performed as described in Example 21 except that the temperature was heated to 80° C. instead of 100° C. The reaction yield was 22.3%.

Example 28: PDI Production from PDA-HCl with Phosgene at 80° C. with TMEDA/Chlorobenzene as Solvent The phosgenation reaction was performed as described in Example 22 except that the temperature was heated to 80° C. instead of 100° C. The reaction yield was 16.5%.

Example 29: PDI Production from PDA-HCl with Phosgene at 80° C. with TMEDA/Toluene as Solvent The phosgenation reaction was performed as described in Example 23 except that the temperature was heated to 80° C. instead of 100° C. The reaction yield was 8.2%.

Example 30: PDI Production from PDA-HCl with Phosgene at 80° C. with Pyridine/Chlorobenzene as Solvent The phosgenation reaction was performed as described in Example 24 except that the temperature was heated to 80° C. instead of 100° C. The reaction yield was 21.9%.

Example 31: PDI Production from PDA-HCl with Phosgene at 80° C. with Pyridine/Toluene as Solvent The phosgenation reaction was performed as described in Example 25 except that the temperature was heated to 80° C. instead of 100° C. The reaction yield was 9.9%.

Example 32: PDI Production from PDA-HCl with Phosgene at 50° C. then 80° C. with TMEDA as Solvent The phosgenation reaction was performed as described in Example 20 except that the temperature was held at 50° C. for 4 h, and then at 80° C. for 12.7 h (instead of at 100° C.). The reaction yield was 16.4%.

Example 33: PDI Production from PDA-HCl with Phosgene at 50° C. then 80° C. with Pyridine as Solvent The phosgenation reaction was performed as described in Example 21 except that the temperature was held at 50° C. for 4 h, and then at 80° C. for 12.7 h (instead of at 100° C.). The reaction yield was 21.5%.

Example 34: PDI Production from PDA-HCl with Phosgene at 50° C. then 80° C. with TMEDA/Chlorobenzene as Solvent The phosgenation reaction was performed as described in Example 22 except that the temperature was held at 50° C. for 4 h, and then at 80° C. for 12.7 h (instead of at 100° C.). The reaction yield was 17.1%.

Example 35: PDI Production from PDA-HCl with Phosgene at 50° C. then 80° C. with TMEDA/Toluene as Solvent The phosgenation reaction was performed as described in Example 23 except that the temperature was held at 50° C. for 4 h, and then at 80° C. for 12.7 h (instead of at 100° C.). The reaction yield was 7.9%.

Example 36: PDI Production from PDA-HC with Phosgene at 50° C. then 80° C. with Pyridine/Chlorobenzene as Solvent The phosgenation reaction was performed as described in Example 24 except that the temperature was held at 50° C. for 4 h, and then at 80° C. for 12.7 h (instead of at 100° C.). The reaction yield was 22.3%.

Example 37: PDI Production from PDA-HCl with Phosgene at 50° C. then 80° C. with Pyridine/Toluene as Solvent The phosgenation reaction was performed as described in Example 25 except that the temperature was held at 50° C. for 4 h, and then at 80° C. for 12.7 h (instead of at 100° C.). The reaction yield was 8.6%.

Example 38: PDI Production from PDA-HCl Salt with Triphosgene at Temperatures of Up to 170° C.

87.5 g (0.5 mol) of PDA-HCl and 100 g of dichlorobenzene were mixed in a 2 L three-necked flask. 3,000 g (10.1 mol) of triphosgene was dissolved in 900 g of dichlorobenzene and slowly added to the three-necked flask at 170° C. The tail gas was quenched with a 10% sodium hydroxide solution and the total reaction time was 6 h. Samples were taken and the reaction yield was 68%. Gas chromatography results are shown in FIG. 5.

Example 39: PDI Production from PDA-HCl Salt with Triphosgene at 100° C. with TMEDA/Chlorobenzene/Dichlorobenzene as Solvent In a 5 L three-necked flask, a solution of 116 g (1 mol) TMEDA in 500 g chlorobenzene was added dropwise to a solution of 1,483 g (5 mol) triphosgene in 3,000 g of dichlorobenzene at a rate of 5 g/min at 50° C. The phosgene gas generated was bubbled to another three-necked flask containing a solution of 87.5 g (0.5 mol) PDA-HCl and 875 g TMEDA at 100° C. The tail gas was quenched with a 10% sodium hydroxide solution. After the reaction was completed, the flask was cooled to 25° C. and samples were taken. The reaction yield was 15.2%. Gas chromatography results are shown in FIG. 6.

Example 40: PDI Production from PDA-HCl Salt with Triphosgene at 100° C. with TMEDA/Chlorobenzene/Dichlorobenzene as Solvent In a 5 L three-necked flask, a solution of 116 g (1 mol) TMEDA in 500 g chlorobenzene was added dropwise to a solution of 1,483 g (5 mol) triphosgene in 3,000 g of dichlorobenzene at a rate of 5 g/min at 50° C. The phosgene gas generated was bubbled to another three-necked flask containing a solution of 87.5 g (0.5 mol) PDA-HCl, 1,050 g chlorobenzene and 116 g (1 mol) TMEDA at 100° C. The tail gas was quenched with a 10% sodium hydroxide solution. After the reaction was completed, the flask was cooled to 25° C. and samples were taken. The reaction yield was 16.3%.

Example 41: PDI Production from PDA-HCl Salt with Triphosgene at 100° C. with Pyridine/chlorobenzene/Dichlorobenzene as Solvent In a 5 L three-necked flask, a solution of 79 g (1 mol) pyridine in 500 g chlorobenzene was added dropwise to a solution of 1,483 g (5 mol) triphosgene in 3,000 g of dichlorobenzene at a rate of 5 g/min at 50° C. The phosgene gas generated was bubbled to another three-necked flask containing a solution of 87.5 g (0.5 mol) PDA-HCl, 1,050 g chlorobenzene and 79 g (1 mol) pyridine at 100° C. The tail gas was quenched with a 10% sodium hydroxide solution. After the reaction was completed, the flask was cooled to 25° C. and samples were taken. The reaction yield was 31.4%. Gas chromatography results are shown in FIG. 7.

Example 42: PDI Production from PDA-HCl Salt with Triphosgene at 100° C. with Pyridine/Chlorobenzene as Solvent In a 5 L three-necked flask, a solution of 79 g (1 mol) pyridine in 500 g chlorobenzene was added dropwise to a solution of 1,483 g (5 mol) triphosgene in 3,000 g of chlorobenzene at a rate of 5 g/min at 50° C. The phosgene gas generated was bubbled to another three-necked flask containing a solution of 87.5 g (0.5 mol) PDA-HCl and 875 g of pyridine at 100° C. The tail gas was quenched with a 10% sodium hydroxide solution. After the reaction was completed, the flask was cooled to 25° C. and samples were taken. The reaction yield was 55.6%.

Example 43: PDI Production from PDA-HCl Salt with Triphosgene at 80° C. with Pyridine/Chlorobenzene/Dichlorobenzene as Solvent In a 5 L three-necked flask, a solution of 79 g (1 mol) pyridine in 500 g chlorobenzene was added dropwise to a solution of 1,483 g (5 mol) triphosgene in 3,000 g of dichlorobenzene at a rate of 5 g/min at 50° C. The phosgene gas generated was bubbled to another three-necked flask containing a solution of 87.5 g (0.5 mol) PDA-HCl, 1,050 g chlorobenzene and 79 g (1 mol) pyridine at 80° C. The tail gas was quenched with a 10% sodium hydroxide solution. After the reaction was completed, the flask was cooled to 25° C. and samples were taken. The reaction yield was 20.3%.

Example 44: PDI Production from PDA-HCl Salt by Triphosgene Direct Addition at 50° C. then 80° C. with pyridine/chlorobenzene as solvent In a 5 L three-necked flask, a solution of 741.5 g (2.5 mol) triphosgene in 1,500 g chlorobenzene was added dropwise to a solution of 87.5 g (0.5 mol) PDA-HCl, 1,050 g chlorobenzene and 79 g (1 mol) pyridine at 30-35° C. After the addition, the reaction mixture was heated up to 50° C. and held for 1 h. Subsequently, the reaction temperature was raised to 80° C. and held for a further 3 h. After the reaction, the reaction flask was cooled to 25° C. and samples were taken. The reaction yield was 20.9%. Gas chromatography results are shown in Table 1.

Example 45: PDI Production from PDA-HCl Salt by Triphosgene Direct Addition at 50° C. then 80° C., 110° C., 120° C. with Pyridine (2 Eq)/Chlorobenzene as Solvent In a 5 L three-necked flask, a solution of 222 g (0.75 mol) triphosgene in 1,500 g chlorobenzene was added dropwise to a solution of 87.5 g (0.5 mol) PDA-HCl, 1,050 g chlorobenzene and 79 g (1 mol) pyridine at 30-35° C. After the addition, the reaction mixture was heated up to 50° C. and held for 1 h. No reaction occurred as indicated by the GC analysis. Then, the reaction temperature was raised to 80° C. and held for a further 3 h. The reaction yield was 12.1%. The reaction temperature was further raised to 110° C. and held for another 3 h. The reaction yield was 22.6%. Finally, the reaction temperature was raised to 120° C. and held for a further 3 h. The reaction yield was 22.7%. Dark polymeric material began to appear at 90° C.

Example 46: PDI Production from PDA-HCl Salt by Triphosgene Direct Addition at 50° C. then 80° C., 110° C., 120° C. with Pyridine (6 Eq)/Chlorobenzene as Solvent In a 5 L three-necked flask, a solution of 222 g (0.75 mol) triphosgene in 1,500 g chlorobenzene was added dropwise to a solution of 87.5 g (0.5 mol) PDA-HCl, 1,050 g chlorobenzene and 237 g (3 mol) pyridine at 30-35° C. After the addition, the reaction mixture was heated up to 50° C. and held for 1 h. No reaction occurred as indicated by the GC analysis. Subsequently, the reaction temperature was raised to 80° C. and held for a further 3 h. The reaction yield was 18.1%. Then, the reaction temperature was further raised to 110° C. and held for another 3 h. The reaction yield was 80.2%. Finally, the reaction temperature was raised to 120° C. and held for a further 3 h. The reaction yield was 80.2%. Dark polymeric material began to appear at 90° C.

Example 47: Overview of Examples 13-46

Example 13 reproduces a conventional industrial process for producing PDI, which involves many labor-intensive steps, is associated with the production of noxious fumes from working with PDA in its free base form, utilizes relatively large amounts of dangerous phosgene gas, and requires high temperatures (e.g., above 170° C.) to obtain reasonable yields.

Example 14 describes a phosgenation reaction that is analogous to the conventional process described in Example 13, except starting from a PDA salt solution (PDA-HCl) instead of PDA free base. Referring to Table 1, while the yield in Example 14 was 88.1% and produced PDI with acceptably high purity (+++++), the entire process consumed a relatively high amount of phosgene (41.4 equivalents), required maintaining high reaction temperatures (170° C.) for an extended period of time (12 hours) with the entire reaction occurring over 13 hours, and produced an undesirable dark insoluble polymeric material at the bottom of the flask (**). The experiments described in Examples 15-46 explore different approaches to improve the production of PDI starting from PDA-HCl, as discussed below. More specifically, objectives included maintaining a reasonably high yield and purity while seeking to: reduce the amount of phosgene consumed, reducing the maximal temperatures required in the process, reducing the entire reaction time, and/or reducing the amount of dark insoluble polymeric material by-product.

Referring to Table 1, Example 15 shows that increasing the maximal reaction temperature to 210° C. resulted in a significant drop in yield (from 88.1% to 56.2%), decreased purity (+++), and a higher amount of the dark polymeric material (***). Initial attempts to decrease the maximal reaction temperature to 130° C. resulted in yields of under 10% (Examples 16-19), even despite the presence of primary amine base (analine) as a potential catalyst (Example 19).

Examples 20-37 and 39-45 show that, with phosgene amounts ranging from 4.5 to 30 equivalents, carrying out the reactions in the presence of a tertiary amine (TMEDA or pyridine), either undiluted or diluted with an inert solvent, lowered the temperatures required for PDI production. However, yields were mostly below 50% and overall purity suffered, with many by-products resulting from unwanted side reactions being visible by GC analysis of the reaction solution (see Tables 1 and 2). Interestingly, comparing Examples 20 & 22, 21 & 24, 26 & 28, 27 & 30, 32 & 34, and 33 & 36 suggests that using excess amounts of tertiary amine was not generally beneficial in terms of yield or purity.

Comparing Examples 43 and 44 suggests that similar yields can be obtained with reduced amounts of phosgene and pyridine if the reaction is initially carried out at a lower temperature (50° C.), favoring formation of intermediates (confirmed by GC). Comparing Examples 44 and 45 shows reducing the amount of phosgene in Example 45 to only 4.5 equivalents decreased yield from 20.9% to 12.1% at 80° C., but that yield was increased to 22.6% by increasing the maximal temperature to 110° C. Example 45 also shows that increasing the temperature to 120° C. did not further improve yield, which is an observation also shown in Example 46.

Example 46 differs from Example 45 only in that the amount of pyridine was increased from 2 equivalents to 6 equivalents. Strikingly, as shown in Table 2, changing this single reaction parameter dramatically increased yield (80.2%), increased purity (+++++), and resulted in minimal accumulation of insoluble dark polymeric material in the reaction solution (*). These results suggest that: (1) the equivalents of tertiary amine must be sufficient enough or both yield and overall purity will be low; (2) in the presence of sufficient equivalents of tertiary amine, the yield increases with the increase of temperature and will not significantly change when the temperature is above 110° C.; and (3) for 1 equivalent of PDA-HCl, 1.5 equivalents of triphosgene (or 4.5 equivalents of phosgene) is sufficient for PDI production.

Thus, the PDI production process described in Example 46 achieved a similar yield and purity to the more conventional process of Example 14, but reduced the amount of phosgene required by almost 90% (40.4 eq to 4.5 eq), reduced the maximal temperature by 60° C. (170° C. to 110° C.), reduced the overall reaction time by about 50% (13.7 h to 7 h), and decreased the amount of insoluble dark polymeric material by-product (** to *).

REFERENCES

Cotarca et al., "Bis(trichloromethyl)carbonate (BTC, Triphosgene): A Safer Alternative to Phosgene?", *Organic Process Research & Development* (2017), 21: 1439-1446.

Qin et al., "Method for Purifying 1,5-Pentanediamine and 1,5-Pentanediamine", European patent application No. 14908171.3 published as EP 3235804.

Sambrook et al. (2001). Molecular Cloning: A Laboratory Manual, Third Edition, Sambrook and Russell, Cold Spring Harbor Laboratory Press, 3rd Edition.

The invention claimed is:

1. A process for producing 1,5-pentamethylene diisocyanate (PDI) from a cadaverine salt, the process comprising:

(a) providing a phosgene source;

(b) providing a solution comprising a cadaverine salt dissolved in an inert solvent in the presence of a tertiary amine base; and (c) subjecting the solution to a liquid-phase phosgenation reaction to convert the cadaverine to PDI, the phosgenation reaction comprising a step of maintaining the reaction at a temperature range between 100° C. and 120° C. to achieve a desired threshold yield of PDI, wherein the tertiary amine base enables the phosgenation reaction to occur to completion at said temperature range.

2. The process of claim 1, wherein the phosgenation reaction temperature in step (c) does not exceed about 119° C.

3. The process of claim 1, wherein the phosgenation reaction in (c) comprises a step of maintaining the reaction at temperatures between 100 and 115° C. to achieve a threshold yield of PDI.

4. The process of claim 1, wherein the phosgenation reaction in (c) is maintained at a temperature range between 100° C. and 120° C. is for 1.5 to 6 hours.

5. A process for producing 1,5-pentamethylene diisocyanate (PDD) from a cadaverine salt, the process comprising:

(a) providing a phosgene source;

(b) providing a solution comprising a cadaverine salt dissolved in an inert solvent in the presence of a tertiary amine base; and (c) subjecting the solution to a liquid-phase phosgenation reaction to convert the cadaverine to PDI, wherein the phosgenation reaction is a multistage phosgenation reaction comprising at least a first stage in which the solution is heated to a first temperature such that the cadaverine reacts with phosgene from the phosgene source to produce a dicarbamoyl chloride intermediate, and a subsequent second stage in which the solution is further heated to a second temperature higher than the first temperature to subject the dicarbamoyl chloride intermediate to dehydrochlorination, wherein the second stage comprises said step of maintaining the reaction at temperatures between 100° C. and 120° C. for a sufficient time to achieve a threshold yield of PDI, wherein the amounts of the phosgene source and/or tertiary amine base reactants employed in the multistage phosgenation reaction is lower than the amounts required to achieve the same PDI yield as a corresponding single-stage phosgenation reaction occurring only at the second temperature, wherein the tertiary amine base enables the phosgenation reaction to occur to completion at said temperature range.

6. The process of claim 5, wherein the first temperature is from about 30 to 65° C. and wherein the first stage comprises maintaining the solution at the first temperature for 0.5 to 3 hours.

7. The process of claim 5, wherein the second temperature is higher than the first temperature by at least 10° C.

8. The process of claim 1, wherein the process employs 3 to 30 mols of phosgene per mole of cadaverine salt.

9. The process of claim 1, wherein the process employs at least 4 mols of tertiary amine base per mole of cadaverine salt.

10. The process of claim 1, wherein the cadaverine salt is a bio-based cadaverine salt obtained from fermentation and/or enzymatic conversion, the enzymatic conversion occurring via an immobilized whole (intact) cell biocatalyst to reduce cyclic compounds from cell lysis components.

11. The process of claim 10, wherein the fermentation is a fermentation of a microorganism engineered to produce cadaverine, and the enzymatic conversion is the one from lysine.

12. The process of claim 1, wherein the cadaverine salt provided is produced without distillation, or was not otherwise subjected to temperatures conducive to the formation of cyclic compounds, wherein the cyclic compounds are selected from one or more in a group consisting of 2,3,4,5-tetrahydropyridine [THP]; piperidine; 2-(aminomethyl)-3,4,5,6-tetrahydropyridine; 1-piperidinecarbonyl chloride; or 1(2H)-pyridinecarbonylchloride.

13. The process of claim 1, wherein the content of THP or other cyclic compounds in the cadaverine salt is below 0.1 wt %.

14. The process of claim 1, wherein the cadaverine salt is cadaverine dihydrochloride.

15. The process of claim 1, wherein the tertiary amine base is a heterocyclic amine or a tertiary amine base having an $sp^2$-hybridized N atom.

16. The process of claim 1, wherein the tertiary amine base is pyridine.

17. The process of claim 1, wherein the insert solvent comprises or consists of chlorobenzene, dichlorobenzene, toluene, nitrobenzene, or any mixture thereof.

18. The process of claim 1, wherein the insert solvent is a solvent or solvent mixture having a boiling point of at least 120° C.

19. The process of claim 1, wherein the process is a one-pot synthesis in which the cadaverine salt and phosgene source are slowly combined in the inert solvent in the presence of the tertiary amine base in a single vessel and subsequently heated to begin the phosgenation reaction.

20. The process of claim 1, wherein the PDI produced has a content of THP or other cyclic compounds of below 0.1 wt % before being subject to one or more distillation steps.

* * * * *

SEQUENCE LISTING

```
<160> NUMBER OF SEQ ID NOS: 2

<210> SEQ ID NO 1
<211> LENGTH: 2148
<212> TYPE: DNA
<213> ORGANISM: Escherichia coli BW25113

<400> SEQUENCE: 1

atgaacgtta ttgcaatatt gaatcacatg ggggtttatt ttaaagaaga acccatccgt      60

gaacttcatc gcgcgcttga acgtctgaac ttccagattg tttacccgaa cgaccgtgac     120

gacttattaa aactgatcga aaacaatgcg cgtctgtgcg gcgttatttt tgactgggat     180

aaatataatc tcgagctgtg cgaagaaatt agcaaaatga acgagaacct gccgttgtac     240

gcgttcgcta atacgtattc cactctcgat gtaagcctga atgacctgcg tttacagatt     300

agcttctttg aatatgcgct gggtgctgct gaagatattg ctaataagat caagcagacc     360

actgacgaat atatcaacac tattctgcct ccgctgacta aagcactgtt taaatatgtt     420

cgtgaaggta aatatacttt ctgtactcct ggtcacatgg gcggtactgc attccagaaa     480

agcccggtag gtagcctgtt ctatgatttc tttggtccga ataccatgaa atctgatatt     540

tccatttcag tatctgaact gggttctctg ctggatcaca gtggtccaca caaagaagca     600
```

```
gaacagtata tcgctcgcgt ctttaacgca gaccgcagct acatggtgac caacggtact    660
tccactgcga acaaaattgt tggtatgtac tctgctccag caggcagcac cattctgatt    720
gaccgtaact gccacaaatc gctgacccac ctgatgatga tgagcgatgt tacgccaatc    780
tatttccgcc cgacccgtaa cgcttacggt attcttggtg gtatcccaca gagtgaattc    840
cagcacgcta ccattgctaa gcgcgtgaaa gaaacaccaa acgcaacctg gccggtacat    900
gctgtaatta ccaactctac ctatgatggt ctgctgtaca acaccgactt catcaagaaa    960
acactggatg tgaaatccat ccactttgac tccgcgtggg tgccttacac caacttctca   1020
ccgatttacg aaggtaaatg cggtatgagc ggtggccgtg tagaagggaa agtgatttac   1080
gaaacccagt ccactcacaa actgctggcg gcgttctctc aggcttccat gatccacgtt   1140
aaaggtgacg taaacgaaga aacctttaac gaagcctaca tgatgcacac caccacttct   1200
ccgcactacg gtatcgtggc gtccactgaa accgctgcgg cgatgatgaa aggcaatgca   1260
ggtaagcgtc tgatcaacgg ttctattgaa cgtgcgatca aattccgtaa agagatcaaa   1320
cgtctgagaa cggaatctga tggctggttc tttgatgtat ggcagccgga tcatatcgat   1380
acgactgaat gctggccgct gcgttctgac agcacctggc acggcttcaa aaacatcgat   1440
aacgagcaca tgtatcttga cccgatcaaa gtcaccctgc tgactccggg gatggaaaaa   1500
gacggcacca tgagcgactt tggtattccg gccagcatcg tggcgaaata cctcgacgaa   1560
catggcatcg ttgttgagaa aaccggtccg tataacctgc tgttcctgtt cagcatcggt   1620
atcgataaga ccaaagcact gagcctgctg cgtgctctga ctgactttaa acgtgcgttc   1680
gacctgaacc tgcgtgtgaa aaacatgctg ccgtctctgt atcgtgaaga tcctgaattc   1740
tatgaaaaca tgcgtattca ggaactggct cagaatatcc acaaactgat tgttcaccac   1800
aatctgccgg atctgatgta tcgcgcattt gaagtgctgc cgacgatggt aatgactccg   1860
tatgctgcat tccagaaaga gctgcacggt atgaccgaag aagtttacct cgacgaaatg   1920
gtaggtcgta ttaacgccaa tatgatcctt ccgtacccgc cgggagttcc tctggtaatg   1980
ccgggtgaaa tgatcaccga agaaagccgt ccggttctgg agttcctgca gatgctgtgt   2040
gaaatcggcg ctcactatcc gggctttgaa accgatattc acggtgcata ccgtcaggct   2100
gatggccgct ataccgttaa ggtattgaaa gaagaaagca aaaaataa                2148
```

<210> SEQ ID NO 2
<211> LENGTH: 715
<212> TYPE: PRT
<213> ORGANISM: Escherichia coli BW25113

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95
```

```
Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
```

-continued

```
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715
```